United States Patent [19]

Crutchfield et al.

[11] 4,384,969

[45] May 24, 1983

[54] NOVEL SURFACTANTS USEFUL IN DETERGENT COMPOSITIONS

[75] Inventors: Marvin M. Crutchfield, Creve Coeur; James M. Mayer, Maryland Heights, both of Mo.

[73] Assignee: Monsanto Company, St. Louis, Mo.

[21] Appl. No.: 362,205

[22] Filed: Mar. 26, 1982

[51] Int. Cl.$^3$ .......................... C07C 69/66; C11D 3/04

[52] U.S. Cl. .................................. 252/89.1; 252/135; 252/558; 560/180

[58] Field of Search .............. 560/180; 252/89.1, 135, 252/558

[56] References Cited

U.S. PATENT DOCUMENTS

| | | | |
|---|---|---|---|
| 2,327,652 | 8/1943 | Kyrides | 260/36 |
| 2,450,333 | 9/1948 | DeGroote et al. | 252/405 |
| 2,469,317 | 5/1949 | Shokal et al. | 167/24 |
| 2,559,521 | 7/1951 | Smith et al. | 260/484 |
| 3,956,383 | 5/1976 | Krause et al. | 560/180 |
| 3,994,959 | 11/1976 | Schneider | 560/180 |
| 4,228,300 | 10/1980 | Lannert | 560/180 |

*Primary Examiner*—Mary F. Downey
*Attorney, Agent, or Firm*—R. C. Griesbauer; J. C. Logomasini; A. H. Cole

[57] ABSTRACT

Novel monoalkyl oxybisacetates are attractively useful as surfactants, and particularly in detergent compositions.

12 Claims, No Drawings

NOVEL SURFACTANTS USEFUL IN DETERGENT COMPOSITIONS

BACKGROUND OF THE INVENTION

Surfactants (surface active substances which reduce the surface tension of water) are widely used, e.g. as wetting agents, in detergent compositions, in cosmetics, and in various other products. Because surfactants having different properties are needed for a variety of applications, new surfactants are highly desirable. As just one of many possible examples, a major problem in modern laundries is the deterioration of appearance of polyester-containing fabrics after continued washing, and effective surfactants are among the best approaches to improving the performance of detergent compositions in cleaning of such fabrics.

Accordingly, an object of this invention is to provide a class of novel compounds that are useful as surfactants. Another object is a class of detergent compositions having improved cleaning performance.

SUMMARY OF THE INVENTION

This invention provides a class of novel compounds which are monoalkyl oxybisacetates. In preferred embodiments, these compounds have the formula $$C_nH_{2n+1}-O\overset{\overset{\displaystyle O}{\|}}{C}-CH_2-O-CH_2-\overset{\overset{\displaystyle O}{\|}}{C}-OM$$

wherein M is hydrogen or alkali metal and n is an integer from about 12 to about 14 when M is alkali metal and from about 10 to about 16 when M is hydrogen. Also provided by the invention are improved cleaning compositions comprising a detergent builder and such a monoalkyl oxybisacetate.

PRIOR ART

Various esters of diglycolic acid have been disclosed as useful in lubricants in U.S. Pat. Nos. 2,559,521 issued July 3, 1951 to P. V. Smith et al, as insecticides in 2,469,317 issued May 3, 1949 to E. C. Shokal et al, as plasticizers in 2,327,652 issued Aug. 24, 1943 to L. B. Kyrides, and as surfactants or demulsifiers in 2,450,333 issued in 1948 to M. DeGroote et al.

DETAILED DESCRIPTION OF THE INVENTION

The novel compounds of this invention are monoalkyl oxybisacetates which are useful as surfactants. Those represented by the foregoing formula are esteracids (half-esters) and the alkali metal (preferably sodium, potassium or lithium) salts thereof. Advantageously for use with laundry detergent compositions, both the half-esters and their alkali metal salts are white solids which are colorless when dissolved in water.

Superior surfactant properties are generally provided when M in the foregoing formula is hydrogen or sodium. The terminal alkyl constitutent of such compounds can be branched but is usually preferably unbranched. When M in that formula is alkali metal, the number of carbon atoms in the terminal alkyl constituent is desirably from about 12 to about 14, and usually most desirably about 12; when M in that formula is hydrogen, the number of carbon atoms in the terminal alkyl constituent is most desirably from about 10 to about 16, generally more desirably from about 12 to about 14, and usually most desirably about 12.

The half-esters of this invention can be prepared by reaction of 1,4-dioxane-2,6-dione (diglycolic anhydride) with an alkanol providing the desired terminal alkyl group. The corresponding alkali metal salts can be prepared by reacting such half-esters with an appropriate alkali metal salt (e.g. bicarbonate) or hydroxide. The following examples of such preparations and detergent compositions containing the resulting monoalkyl oxybisacetates are illustrative only and do not imply any limitation on the scope of this invention. Percentages herein are by weight unless indicated otherwise.

EXAMPLE 1—DODECYL HYDROGEN OXYBISACETATE 18.6 g n-dodecanol was dissolved in 25 ml pyridine on a steam bath. When 11.6 g of 1,4-dioxane-2,6-dione was added with stirring, the mixture quickly reached 80° C. After 5 minutes the solution was allowed to cool to room temperature and, after 2 hours, was poured into 200 ml 1 N HCl. The gel which precipitated was extracted with 300 ml ether, washed three times, with 0.1 N HCl and dried over $Na_2SO_4$. The ether was evaporated and the resulting clear oil was taken up in petroleum ether. Agitation and cooling under nitrogen precipitated a product which was separated by filtration. The remaining solution was diluted to 250 ml with petroleum ether for precipitation of a second crop. The yield totalled 18.1 g of a white crystalline solid that melted at 57°-59° C. and was soluble in acetone, chloroform, ether and/or methanol. Elemental analysis indicated 56.8% C; 8.5% H (Calc. 56.7% C; 8.5% H).

EXAMPLE 2—DODECYL SODIUM OXYBISACETATE 2 g of the half-ester prepared in Example 1 and 0.6 g $NaHCO_3$ were dissolved in 25 ml methanol. After partial evaporation of the mixture (non-homogeneous), it was mixed with more methanol. This was followed by further evaporation and then a nitrogen purge, leaving a solid which, on drying, provided a white powder. Elemental analysis indicated 57.0% C; 8.7% H (Calc. 59.2% C; 9.0% H).

EXAMPLE 3—TETRADECYL HYDROGEN OXYBISACETATE

A procedure essentially like that in Example 1 using 42.9 g n-tetradecanol, 23.2 g 1,4-dioxane-2,6-dione and 100 ml pyridine yielded 34.6 g of a white crystalline solid that melted at 60°-63° C. and was soluble in acetone, chloroform, ether and/or methanol. Elemental analysis indicated 65.7% C; 10.6% H (Calc. 65.4% C; 10.4% H).

EXAMPLE 4—TETRADECYL SODIUM OXYBISACETATE 0.25 g anhydrous sodium bicarbonate was added to 1 g of the product of Example 3 and 25 ml methanol. Mixing followed by evaporation on a rotary evaporator with a stream of $N_2$ left a precipitate which, on drying, provided a white powder. Elemental analysis indicated 61.2% C; 9.3% H (Calc. 61.3% C; 9.4% H).

EXAMPLE 5—DECYL HYDROGEN OXYBISACETATE

Using 158.3 g n-decyl alcohol, 116.1 g 1,4-dioxane-2,6-dione and 15 ml pyridine, the procedure of Example 1 was essentially duplicated, after which the mixture was passed into 200 ml 1 N HCl. This was extracted with 100 ml ether. The organic phase was washed with 50 ml saturated NaCl, dried over $Na_2SO_4$ and evaporated on a rotary evaporator, leaving 26.4 g of a colorless oil which solidified as a white solid that melted at 46°-48° C. and was soluble in acetone, chloroform, ether and/or ethanol. Elemental analysis indicated 61.5% C; 9.5% H (Calc. 61.5% C; 9.5% H).

EXAMPLE 6—HEXADECYL HYDROGEN OXYBISACETATE 24.2 g n-hexadecanol was dissolved in 25 ml pyridine at 40° C. 11.6 g 1,4-dioxane-2,6-dione was added in five equal portions, letting each dissolve before adding more. After 30 minutes at 40° C., the mixture was removed, cooled and poured into 250 ml 2 N HCl, giving an oily precipitate. 150 ml ether was added with agitation. The aqueous layer was extracted again with 50 ml ether. The combined ether layers were extracted twice with 100 ml 0.1 N HCl, and the ether was evaporated to 50 ml, forming a solid precipitate. Dilution to 200 ml with pentane provided a white slurry which, on filtration and drying, gave a white crystalline solid that melted at 68°-69° C. and was soluble in acetone, chloroform, ether and/or methanol. Elemental analysis indicated 67.0% C; 10.6% H (Calc. 67.0% C; 10.7% H).

The compounds prepared in the preceding Examples have been found useful as surfactants, and particularly for use in detergent compositions such as those having laundry applications, e.g. for cleaning of polyester-containing or other fabrics. In many instances, those compositions are advantageously formulated with detergent builders selected from the condensed phosphates and/or their alkali metal salts, preferably sodium or potassium tripolyphosphate. Most commonly, such compositions contain from about 5% to about 40% (preferably from about 10% to about 30%) surfactant.

As shown hereinafter, the compounds of this invention, when used in combination with conventional surfactants such as linear alkylbenzene sulfonates, provide attractive levels of surfactant effectiveness, especially when M is hydrogen and n is about 12 in the foregoing formula. In such combinations, the alkylbenezene sulfonates are desirably those in which the sulfonated benzene group is attached to a non-terminal carbon atom of the linear alkyl chain and which have an average molecular weight between about 300 and about 360. Normally, the weight ratio of the oxybisacetate to the other surfactant(s) in such compositions is from about 4:1 to about 1:4 (most advantageously from about 2:1 to about 1:2).

SURFACTANT PERFORMANCE DETERMINATIONS

Compounds of this invention were tested for soil removal performance in two detergent compositions, each containing 50% sodium tripolyphosphate, 20% surfactant, 17% sodium sulfate, 12% RU Silicate and 1% carboxymethyl cellulose. In System A, a compound of this invention was used as the sole surfactant, while in System B the surfactant was a 1:1 mixture by weight of a compound of this invention and linear alkylbenzene sulfonates having an average molecular weight of 330. The 20% surfactant level was chosen to provide relatively sensitive detergency results, and the phosphate level was set high enough to protect the surfactants from hardness ions. The remaining ingredients and their levels are typical of those in common detergent compositions.

The tests were carried out using a 65% polyester/35% cotton blend fabric with permanent press finish, a fabric which has previously demonstrated severe soil removal problems. The fabric was soiled with a synthetic sebum composed of airbone particulate soil. Both detergent compositions were used at 0.15% concentration which corresponds to the 1¼ cups per washer load recommended by many detergent manufacturers. A medium wash temperature of 30° C. was used corresponding to that normally recommended for permanent press fabrics. The tests were carried out with deionized water to which 150 ppm of hardness ions (calculated as CaCO3; Ca/Mg=3/2) were added for the tests in Groups I and III, a level typical of medium hard water supplies in the U.S.A. The tests in Group II were carried out without addition of hardness ions. The pH of each test solution was controlled at 10±0.5. The swatches of identically soiled fabric were machine-washed in the solutions for 10 minutes, rinsed and dried, after which detergency performance was calculated as the difference between reflectances of the soiled swatches and washed swatches, as determined with a Gardner Colorimeter. Variations of soil from batch to batch preclude direct comparison of the results in one Test Group with those in any other Test Group. As a standard, however, the sulfonates were used as the sole surfactant in a run directly comparable with those in each Test Group for each detergent composition. Results were as follows:

| Test Group | Surfactant-Oxybisacetate Prepared in Example | Detergent System A (Only Oxybisacetate: Surfactant) | Detergent System B (1:1 Oxybisacetate: Sulfonate) |
|---|---|---|---|
| I (150 ppm Hardness Ions) | 1-Dodecyl Hydrogen | 18.5 | 25.0 |
| | 3-Tetradecyl Hydrogen | 12.2 | 12.6 |
| | 5-Decyl Hydrogen | 8.5 | 15.5 |
| | 6-Hexadecyl Hydrogen | 7.2 | 16.2 |
| | None | 7.1 | 7.3 |
| | (100% Sulfonates) | 29.4 | 24.9 |
| II (No Hardness Ions) | 1-Dodecyl Hydrogen | 30.0 | 33.1 |
| | 6-Hexadecyl Hydrogen | 23.0 | 31.1 |
| | None | 16.6 | 17.0 |
| | (100% Sulfonates) | 32.7 | 31.5 |
| III (150 ppm Hardness Ions) | 2-Dodecyl Sodium | 13.6 | 15.0 |
| | 4-Tetradecyl Sodium | 9.8 | 14.7 |
| | None | 7.6 | 6.6 |
| | (100% Sulfonates) | 24.6 | 23.4 |

What is claimed is:

1. A compound having the structural formula:

$$C_nH_{2n+1}-O\overset{O}{\overset{\|}{C}}-CH_2-O-CH_2-\overset{O}{\overset{\|}{C}}-O-M$$

wherein M is hydrogen or alkali metal and n is an integer from about 12 to about 14 when M is alkali metal and from about 10 to about 16 when M is hydrogen.

2. A compound of claim 1 wherein M is hydrogen.

3. A compound of claim 2 wherein n is from about 12 to about 14.

4. A compound of claim 2 wherein n is about 12.

5. A compound of claim 1 wherein M is alkali metal.

6. A compound of claim 5 wherein M is sodium.

7. A compound of claim 6 wherein n is about 12.

8. A composition comprising a detergent builder and a compound having the structural formula:

$$C_nH_{2n+1}-O\overset{O}{\overset{\|}{C}}-CH_2-O-CH_2-\overset{O}{\overset{\|}{C}}-O-M$$

wherein M is hydrogen or alkali metal and n is an integer from about 12 to about 14 when M is alkali metal and from about 10 to about 16 when M is hydrogen.

9. A composition of claim 8 wherein the builder comprises a condensed phosphate and/or an alkali metal salt thereof.

10. A composition of claim 8 wherein M is hydrogen.

11. A composition of claim 8 wherein n is about 12.

12. A composition of claim 8 further comprising linear alkylbenzene sulfonates having an average molecular weight between about 300 and about 360.

* * * * *